US00PP17529P2

(12) United States Plant Patent
Jepsen

(10) Patent No.: US PP17,529 P2
(45) Date of Patent: Mar. 27, 2007

(54) ***KALANCHOE* PLANT NAMED 'KJ 2003 0855'**

(50) Latin Name: *Kalanchoe blossfeldiana*
Varietal Denomination: KJ 2003 0855

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 55 days.

(21) Appl. No.: 11/146,201

(22) Filed: Jun. 6, 2005

(51) Int. Cl.
*A01H 5/00* (2006.01)

(52) U.S. Cl. ..... Plt./338
(58) Field of Classification Search ..... Plt./338
See application file for complete search history.

(56) References Cited

U.S. PATENT DOCUMENTS

PP9,429 P * 1/1996 Jepsen ..... Plt./340
PP16,088 P2 * 11/2005 Jepsen ..... Plt./335

OTHER PUBLICATIONS

UPOV ROM GTITM Computer Database, GTI Jouve Retrieval Software 2006/05 Citation for 'KJ 2003 0855'.*

* cited by examiner

*Primary Examiner*—Wendy Haas
(74) *Attorney, Agent, or Firm*—C. A. Whealy

(57) ABSTRACT

A distinct cultivar of *Kalanchoe* plant named 'KJ 2003 0855', characterized by its upright plant habit; dark green-colored leaves; golden yellow-colored flowers with more than 20 petals per flower; and excellent postproduction longevity.

1 Drawing Sheet

Botanical designation: *Kalanchoe blossfeldiana.*
Cultivar denomination: 'KJ 2003 0855'.

BACKGROUND OF THE INVENTION

The present invention relates to a new and distinct cultivar of *Kalanchoe* plant, botanically known as *Kalanchoe blossfeldiana,* and hereinafter referred to by the name 'KJ 2003 0855'.

The new *Kalanchoe* is a product of a planned breeding program conducted by the Inventor in Hinnerup, Denmark. The objective of the breeding program was to create new freely-flowering *Kalanchoe* cultivars with large flowers, numerous petals per flower, attractive flower coloration and excellent postproduction longevity.

The new *Kalanchoe* originated from a cross-pollination made in Hinnerup, Denmark, of the *Kalanchoe* cultivar Fame, disclosed in U.S. Plant Pat. No. 9,429, as the female, or seed, parent with the *Kalanchoe* cultivar KJ 2001 1857, not patented, as the male, or pollen, parent. The new *Kalanchoe* was discovered and selected by the Inventor as a single flowering plant within the progeny of the stated cross-pollination grown in a controlled environment in Hinnerup, Denmark.

Asexual reproduction of the new *Kalanchoe* by terminal cuttings at Hinnerup, Denmark, by the Inventor, has shown that the unique features of this new *Kalanchoe* are stable and reproduced true to type in successive generations.

BRIEF SUMMARY OF THE INVENTION

The cultivar KJ 2003 0855 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KJ 2003 0855'. These characteristics in combination distinguish 'KJ 2003 0855' as a new and distinct cultivar:

1. Upright plant habit.
2. Dark green-colored leaves.
3. Golden yellow-colored double flowers with more than 20 petals per flower.
4. Excellent postproduction longevity.

Plants of the new *Kalanchoe* differ primarily from plants of the parent cultivars in petal number and petal coloration.

Plants of the new *Kalanchoe* can be compared to plants of the *Kalanchoe* cultivar KJ 2002 0521, disclosed in U.S. Plant Pat. No. 16,088. Plants of the new *Kalanchoe* differ primarily from plants of the cultivar KJ 2002 0521 in petal number and petal coloration.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.* The photographs were taken under diffuse natural light conditions on a sunny day at approximately noon in Hinnerup, Denmark.

The photograph at the top of the sheet comprises a side perspective view of a typical flowering potted plant of 'KJ 2003 0855'.

The photograph at the bottom of the sheet comprises a top perspective view of a typical flowering plant of 'KJ 2003 0855'.

DETAILED BOTANICAL DESCRIPTION

In the following description, color references are made to The Royal Horticultural Society Colour Chart, 2001 Edition, except where general terms of ordinary dictionary significance are used. Plants used in the photographs and for the following observations and measurements were grown in Hinnerup, Denmark, under commercial practice in a glass-covered greenhouse for about ten to eleven weeks after the start of short day/long night photoperiodic treatment with average temperatures of 20° C. Plants used in the description and photographs were not pinched. Unless otherwise specified, the leaf description represents leaves from a vegetative plant.

Botanical classification: *Kalanchoe blossfeldiana* cultivar KJ 2003 0855.

Parentage:

*Female, or seed, parent.*—*Kalanchoe blossfeldiana* cultivar Fame, disclosed in U.S. Plant Pat. No. 9,429.

*Male, or pollen, parent.*—*Kalanchoe blossfeldiana* cultivar KJ 2001 1857, not patented.

Propagation:

*Type cutting.*—Terminal cuttings.

*Time to produce a rooted young plant.*—About two weeks.

*Root description.*—Numerous, fine, fibrous, and well-branched.

Plant description:

*Form.*—Upright plant habit with numerous compound cymes; freely flowering. Actual plant shape will depend on whether or not plants are pinched (apical terminals removed).

*Branching habit.*—Freely branching. Pinching (removal of terminal apex) is not required but will enhance lateral branch development.

*Plant height at flowering.*—About 25 cm.

*Plant diameter at flowering.*—About 30 cm.

*Foliage description.*—Arrangement: Opposite, simple. Size: Leaf size is reduced after floral induction. Vegetative plants: Length: About 12 cm. Width: About 8.5 cm. Reproductive plants: Length: About 4 cm. Width: About 3 cm. Shape: Elliptic. Apex: Rounded. Base: Obtuse. Margin: Crenate. Aspect: Slightly concave. Texture, upper and lower surfaces: Glabrous; leathery; succulent. Color: Developing and fully expanded foliage, upper surface: 147A. Developing and fully expanded foliage, lower surface: 137A.

Flower description:

*Flower type and habit.*—Double flowers arranged in compound dichasial cymes that arise from leaf axils. Upright flowering stems. Freely flowering. Flowers persistent.

*Natural flowering season.*—Winter to early spring; flower initiation and development can be induced under short day/long night conditions.

*Time to flower.*—In the summer with 20° C. growing temperatures, about ten weeks of short day/long night conditions are required to produce flowering plants. During the winter with supplemental lighting and 20° C. growing temperatures, about eleven weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About one week after the first flower has opened, 20% of the remaining flowers are open.

*Post-production longevity.*—Plants of the new *Kalanchoe* maintain good leaf and flower substance for about five weeks under interior environmental conditions.

*Flower diameter.*—About 1.9 cm.

*Quantity.*—Freely flowering, potentially about 300 flowers per plant.

*Flower buds.*—Shape: Narrowly oblong. Length: About 1 cm. Width: About 5 mm. Color: 20B.

*Petals.*—Quantity: Typically about 25. Length: About 1 cm. Diameter: About 5 mm. Shape: Round obovate. Apex: Cuspidate. Margin: Entire. Texture, upper and lower surfaces: Glabrous, smooth and satiny. Color: When opening and fully opened, upper surface: 14B tinged with 24B. Lower surface: 16C tinged with 23A.

*Reproductive organs.*—Stamens: Stamen number: About 10 to 15. Anther shape: Slightly oblong. Filament color: Green. Pollen color: Yellow. Pistils: Pistil number: About four. Style color: Green. Stigma shape: Round. Ovaries: Superior and four-celled. Ovary size: About 4 mm by 2 mm. Ovary color: Light green.

*Seed/fruit.*—Seed and fruit production has not been observed.

Disease/pest resistance: Resistance to known pathogens and pests common to *Kalanchoe* has not been observed on plants of the new *Kalanchoe* grown under commercial greenhouse conditions.

It is claimed:

1. A new and distinct cultivar of *Kalanchoe* plant named 'KJ 2003 0855', as illustrated and described.

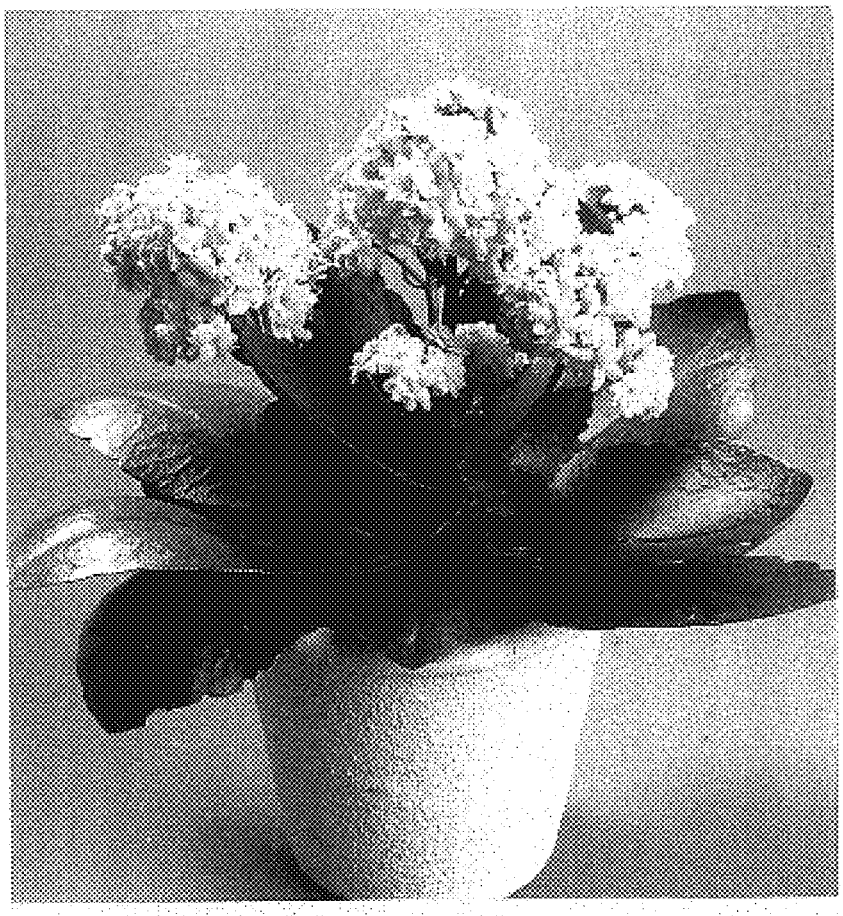
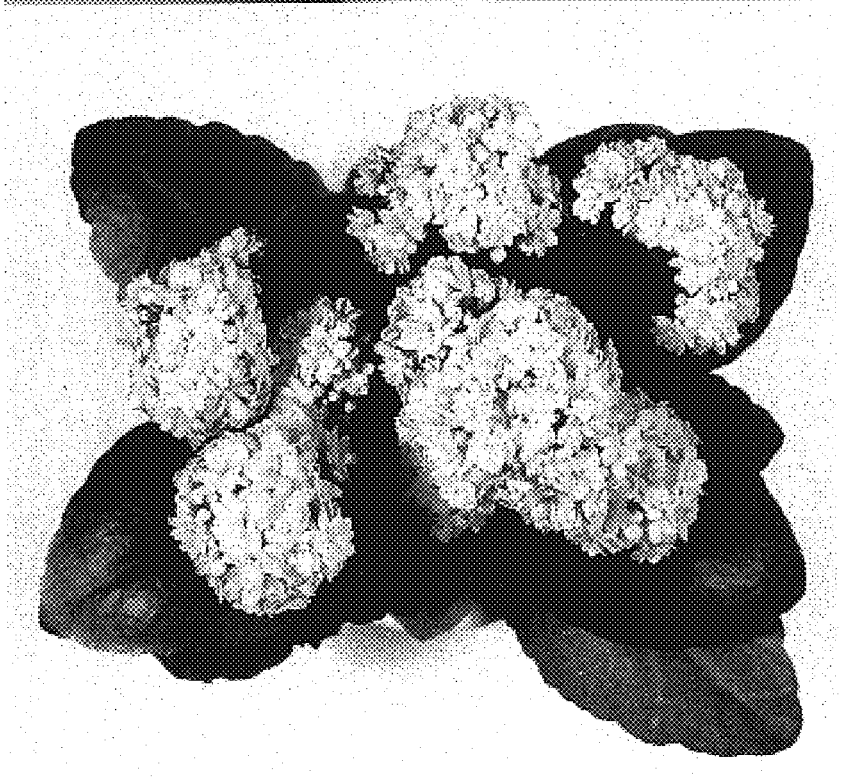

* * * * *